US011378565B2

United States Patent
Preusse et al.

(10) Patent No.: US 11,378,565 B2
(45) Date of Patent: Jul. 5, 2022

(54) METHOD FOR IN-OVO FERTILISATION DETERMINATION AND GENDER DETERMINATION ON A CLOSED EGG

(71) Applicant: Technische Universität Dresden, Dresden (DE)

(72) Inventors: Grit Preusse, Radebeul (DE); Gerald Steiner, Schwarzenberg (DE); Roberta Galli, Dresden (DE); Edmund Koch, Dresden (DE); Christian Schnabel, Dresden (DE)

(73) Assignee: Technische Universität Dresden, Dresden (DE)

( * ) Notice: Subject to any disclaimer, the term of this patent is extended or adjusted under 35 U.S.C. 154(b) by 84 days.

(21) Appl. No.: 16/978,679

(22) PCT Filed: Mar. 8, 2019

(86) PCT No.: PCT/EP2019/055904
§ 371 (c)(1),
(2) Date: Sep. 5, 2020

(87) PCT Pub. No.: WO2019/170887
PCT Pub. Date: Sep. 12, 2019

(65) Prior Publication Data
US 2020/0400640 A1    Dec. 24, 2020

(30) Foreign Application Priority Data
Mar. 9, 2018    (DE) .......................... 102018105512.9

(51) Int. Cl.
*G01N 33/08* (2006.01)
*G01N 21/64* (2006.01)
(Continued)

(52) U.S. Cl.
CPC ......... *G01N 33/08* (2013.01); *G01N 21/6486* (2013.01); *G06K 9/00557* (2013.01); *G06V 10/145* (2022.01); *G06V 10/26* (2022.01)

(58) Field of Classification Search
CPC .... G01N 33/08; G01N 21/6486; G01N 21/31; G06K 9/00557; G06V 10/145; G06V 10/26
See application file for complete search history.

(56) References Cited

U.S. PATENT DOCUMENTS 6,535,277 B2    3/2003   Chalker, II
7,041,439 B2 *  5/2006   Phelps .................... G01N 1/34
                                            435/235.1
(Continued)

FOREIGN PATENT DOCUMENTS

CN    104316473 A    1/2015
DE    102010006161 B3    1/2011
(Continued)

OTHER PUBLICATIONS

Roberta Galli et al, "In Ovo Sexing of Domestic Chicken Eggs by Raman Spectroscopy", Analytical Chemistry, US, vol. 88, No. 17, Sep. 6, 2016 (Sep. 6, 2016), pp. 8657-8663, DOI: 10.1021/acs. analchem.6b01868, ISSN: 0003-2700, XP055378439, abstract, figures.
(Continued)

*Primary Examiner* — Mohamed K Amara
(74) *Attorney, Agent, or Firm* — Michael Soderman (57) ABSTRACT

A method for in-ova fertilisation determination and gender determination on a closed egg. The aim is to specify a method for the in-ovo fertilisation determination and gender determination on a closed egg. This aim is achieved by a method in which a closed egg is positioned, candled and/or illuminated, next an image of the closed egg is recorded, then the captured data are evaluated and the position of the cardiovascular system located in the egg is calculated. A
(Continued)

detection unit is adjusted via the calculated position of the cardiovascular system by means of a positioning unit and subsequently the blood is stimulated, then the blood-specific and blood-foreign absorption spectra are detected and selected, the fertilisation is ascertained and then the spectra containing blood-foreign information are compensated by a compensation method and the spectra are classified for sex determination.

17 Claims, 2 Drawing Sheets

(51) Int. Cl.
*G06K 9/00* (2022.01)
*G06V 10/26* (2022.01)
*G06V 10/145* (2022.01)

(56) References Cited

U.S. PATENT DOCUMENTS

| | | | | |
|---|---|---|---|---|
| 8,624,190 | B2* | 1/2014 | Steiner | G01N 21/552 250/339.08 |
| 9,179,651 | B2* | 11/2015 | McKay | A01K 45/00 |
| 9,835,560 | B2* | 12/2017 | Galli | G01N 33/4833 |
| 10,060,854 | B2* | 8/2018 | Schortgen | G01N 33/085 |
| 10,852,284 | B2* | 12/2020 | Steiner | A01K 43/04 |
| 2012/0318981 | A1* | 12/2012 | Steiner | G01N 21/3563 250/341.2 |
| 2013/0004421 | A1 | 1/2013 | Capala | |
| 2013/0044210 | A1 | 2/2013 | Rozenboim | |
| 2016/0239953 | A1 | 8/2016 | Ngadi et al. | |
| 2017/0205353 | A1* | 7/2017 | Galli | G01N 33/4833 |
| 2019/0383782 | A1* | 12/2019 | Steiner | A01K 45/00 |

FOREIGN PATENT DOCUMENTS

| | | |
|---|---|---|
| DE | 102012016911 B3 | 6/2013 |
| DE | 102014010150 A1 | 1/2016 |
| DE | 102016004051 B3 | 7/2017 |
| JP | 2017227471 A | 12/2017 |
| WO | 2014086335 A1 | 6/2014 |
| WO | 2016131124 A1 | 8/2016 |
| WO | 2017094015 A1 | 6/2017 |
| WO | 2018023105 A1 | 2/2018 |

OTHER PUBLICATIONS

Roberta Galli et al, "In ovo sexing of chicken eggs by fluorescence spectroscopy", Analytical and Bioanalytical Chemistry, Springer, DE, vol. 409, No. 5, Dec. 14, 2016 (Dec. 14, 2016), pp. 1185-1194, DOI: 10.1007/S00216-016-0116-6, ISSN: 1618-2642, XP036142794, abstract, Figs. 1 and 4.

Gerald Steiner et al, "Gender determination of fertilized unincubated chicken eggs by infrared spectroscope imaging", Analytical and Bioanalytical Chemistry, Springer, Berlin, DE, vol. 400, No. 9, Apr. 9, 2011 (Apr. 9, 2011), pp. 2775-2782, DOI: 10.1007/S00216-011-4941-3, ISSN: 1618-2650, XP019909218, the whole document.

Göhler, Doreen; Fischer, Björn; Meissner, Sven: In-ovo sexing of 14-day-old chicken embryos by pattern analysis in hyperspectral images (VIS/NIR spectra): A non-destructive method for layer lines with gender-specific down feather color. In: Poultry Science, vol. 96, 2017, H. 1, pp. 1-4—ISSN 0032-5791 (p); 1525-3171 (e). DOI: 10.2282/ps/pew282. URL: https://academic.oup.com/ps/article-pdf/96/1/1/8497077/pew282.pdf.

Imholt, Dirk; Justus-Liebig-Universität Giessen Department of Vetinary Medicine: Morphometrische Studien an Eiern von Hybrid—und Rassehühnern mit Versuchen zur Detektion einer Beziehung zwischen der Form von Eiern und dem Geschlecht der darin befindlichen Küken: Eine oologische und mathematische Studie. 1. Aufl., Giessen : VVB Laufersweller Verlag, 2010, pp. 1-155.—ISBN 978-3-8359-5545-5. URL : http://geb.uni-giessen.de/geb/volltexte/2010/7760/pdf/ImholtDirk_2010_07_05.pdf.

\* cited by examiner

METHOD FOR IN-OVO FERTILISATION DETERMINATION AND GENDER DETERMINATION ON A CLOSED EGG

CROSS REFERENCE TO RELATED APPLICATIONS

This application is the U.S. national stage of International Application No. PCT/EP2019/055904, filed on 2019 Mar. 8. The international application claims the priority of DE 102018105512.9 filed on 2018 Mar. 9; all applications are incorporated by reference herein in their entirety.

BACKGROUND

The invention refers to fields in process engineering and agriculture and relates to a method for determining fertilization and sex in ovo on a closed egg. By way of example, the method can be used for determining fertilization and sex in ovo, for example for birds' eggs.

A strong negative correlation between egg production and fattening prevents chickens from being used as egg producers and a source of meat at the same time. Thus, breeding over the last decades has led to the rise of specialist lines of chickens, which either allow economical production of high-quality eggs (chickens) or are suitable for efficient meat production (roosters and chickens). While chickens of the fattening lines are also fattened, roosters from the laying lines can only be economically raised and marketed to a very small extent at the present time. This problem affects not only conventional egg production but also the keeping of laying hens according to ecological guidelines. The previously conventional method of killing the male offspring in the laying hen lines immediately after hatching contradicts legal requirements and objectives of animal welfare, and consequently is confronted with ethical and legal concerns at home and abroad. Therefore, there is increased research activity in view of alternatives to killing the male day-old chicks when producing eggs. Invasive and noninvasive processes for sexing fertilized chicken eggs at various incubation time periods have been described previously.

DE 10 2014 010 150 A1 has disclosed a method and an apparatus for sexing fertilized and incubated birds' eggs in ovo by Raman spectroscopy, in which a hole is introduced into the eggshell by way of a laser or a mechanical perforation and the Raman-scattered radiation of the irradiated blood is captured and evaluated by means of an evaluation unit.

A contactless spectroscopic method and an apparatus for optically sexing fertilized and incubated birds' eggs in ovo is described in DE 10 2016 004 051 A1. A hole is likewise introduced into the eggshell and sexing is implemented here by evaluating the Raman-scattered radiation on incubation day 4, which corresponds to an early embryonal stage before the onset of experiencing pain.

A disadvantage of this method is that a hole has to be introduced into the eggshell before the spectroscopic measurement in order to be able to carry out the determination of sex.

The disadvantages of the invasive methods consist in an elevated risk of infection and injury and an increased technical outlay for opening the egg and sealing said egg again.

Galli et al. [Anal Bioanal Chem. 2017, February; 409(5): 1185-1194] describe the sex-specifics of the fluorescence spectra of embryonal chicken blood after the introduction of an opening into the eggshell, which are displayed in the spectral profile and intensity values. According to theory, the structure of a molecule, as a rule, hardly changes due to an electronic transition. Therefore, the excited energetic state has a molecular structure similar to the ground state. The fine structure of the energy levels of ground state and of excited state is very similar, as a rule. Derived from this is the often observed mirror symmetry between the fluorescence emission spectrum and the absorption spectrum in the region of the S1/S0 transitions.

To ensure healthy embryonal development and be able to realize an economically expedient solution using technology, determining the sex on a closed bird's egg at the earliest possible development stage, even in a non-incubated egg, has been sought after for years.

Imholt, D. ("Morphometrische Studien an Eiern von Hybrid-und Rassehühnem mit Versuchen zur Detektion einer Beziehung zwischen der Form von Eiern und dem Geschlecht der darin befindlichen Küken", doctoral thesis, VVB Laufersweiler Verlag, 2010) has disclosed that it was not possible to find a relationship between the shape and size of the egg and the sex of the embryo.

WO 2014 086 335 A1 has disclosed a method and an arrangement for noninvasive, nondestructive identification of molecule-specific and/or biological properties of an inner structure of a biological examination object through an optically opaque barrier, in which the examination object, such as an egg, is not altered; i.e., the eggshell is not opened. Here, the egg is positioned under an array of pulse transmitters and receivers, with the electromagnetic pulses emitted by the pulse transmitters being in the spectral range of 0.01 to 1 THz. The radiation emanating from the examination object is recorded by the receivers and evaluated on a computer. The evaluation is implemented by the computer-assisted comparison of the captured THz-absorption spectra with reference spectra. For the purposes of extracting the relevant individual spectrum of the genetic material of the blastodisc, spectra of the individual components of the bird's egg are calculated and subtracted from the measured integral spectrum. The model is refined within a batch on the basis of adaptive software algorithms. After the measurement of a batch has been completed, the arisen data is evaluated and analyzed using statistical processes under the assumption of expected sex-specific features.

A disadvantage here is that the proportion of the absorption of the blastodisc with the DNA-containing cells is only very low in percentage terms in comparison with the sum of the absorptions of the other egg components (yoke, egg white, shell).

The use of methods known subsumed by "genetic engineering" and the use of transgenic animals connected therewith allow sexing of the fertilized, non-incubated chicken egg.

WO 2017 094 015 A1 has disclosed a method for sexing unhatched birds' eggs, in which at least one reporter gene is integrated in at least one of the sex chromosomes W or Z. The optical signal of this reporter gene, for example initiated by bioluminescence, can be detected through the shell.

Hyperspectral imaging (abbreviated HSI) represents a further process that has been applied to be able to determine the fertilization rate and sex on closed chicken eggs in the earliest possible incubation state. In the hyperspectral imaging method, a spatially resolved and wavelength-resolved detection is used, depending on the question in the spectral ranges of UV (200-400 nm), VIS (400-750 nm), NIR (750-2500 nm) and MIR (2500-10 000 nm), wherein at least 100 points in the spectrum are recorded, as a rule.

US 2013 004 421 A1 has disclosed a hyperspectral process of reflection spectroscopy, which can be used to determine the fertilization rate and the sex of a closed bird's egg. A neural network is trained for evaluating the spectra obtained and the obtained test spectrum is compared to a spectrum library.

CN 104 316 473 A has disclosed a hyperspectral transmission imaging process in the spectral range from 400 to 1000 nm on a closed chicken egg. Mathematical models based on partial least-squares discriminant analysis, PLSDA, or on nonlinear algorithms such as artificial neural networks, ANN, or the support vector machine, SVM, are used in the evaluation of the registered transmission spectra. A disadvantage of this method is that the highest prediction accuracy is only reached at incubation day 10, if the spectral range was reduced to 600 to 900 nm and a region in the center of the egg was selected and the classification of the spectra was implemented on the basis of a neural network.

Göhler, D. et al. "In-ovo sexing of 14-day-old chicken embryos by pattern analysis in hyperspectral images", Poultry Science 96:1-4 (2017), has disclosed an optical method for analyzing the sex of chicken embryos using sex-specific feather coloring in the closed chicken egg during incubation days 11 to 14, and consequently only at a very late stage following the fertilization of the chicken egg.

WO 2016 131 124 A1 discloses a method and an apparatus for characterizing unhatched birds, with the characteristics obtained also containing the fertilization rate and the sex. The data is recorded using an imaging system; the data are evaluated using a feature extractor and a downstream classification.

However, it is known that on day 0 following fertilization, the difference between male and female eggs is only based on the different size of the sex chromosomes W and Z. Thus, DNA exhibits no absorption in the spectral range from 900 to 1700 nm, and so the classification disclosed in this method is based on undescribed differences in the egg components of yoke, egg white and shell. On account of this, the robustness of such a classification on day 0 is assessed as being very susceptible on account of the high natural variability of the eggs, e.g., due to seasonal changes or changes in the feed, the age of the animals or a varying shell thickness.

A disadvantage of the described processes based on hyperspectral imaging is that all naturally varying egg constituents of the respective incubation stage, and hence also the non-sex-specific components as well, are included in the evaluation for determining sex. A further disadvantage of the specified methods consists of sex determination with a high and stable prediction accuracy only being able to be carried out in the case of brown layer chickens (in-ovo color sexing) and/or on incubation day 10 to 14, i.e., in a late fetal stage, in which the embryo certainly feels pain.

SUMMARY

The object of the invention consists in specifying a method for determining fertilization and sex in ovo on a closed egg, which, simultaneously, allows fertilization and sex to be determined in ovo on a closed egg, facilitates the determination of fertilization and sex during incubation time period and facilitates a great accuracy in the fertilization rates and sex determination.

The object is achieved by the invention specified in the claims. Advantageous embodiments of the invention are the subject matter of the dependent claims.

DETAILED DESCRIPTION

According to the invention, the method according to the invention relates to determining fertilization and sex in ovo on a closed egg, comprising the method steps of:
  positioning a closed egg,
  candling and/or illuminating the egg by means of at least one light source using light in the spectrum of visible and/or near-infrared light,
  recording an image of the candled and/or illuminated closed egg by means of an optical recording system and evaluating the captured data of the generated image by means of an evaluation unit,
  calculating the position of the cardiovascular system situated in the egg from the evaluated data of the camera image by means of the evaluation unit,
  setting a detection unit above the calculated position of the cardiovascular system by means of a positioning unit,
  exciting the blood situated in the cardiovascular system by means of an excitation unit,
  detecting and selecting the blood-specific absorption spectra and the blood-extrinsic absorption spectra by means of a capturing unit,
  determining fertilization, wherein the following method steps are performed after fertilization has been established,
  compensating the spectra with blood-extrinsic information by a compensation method by means of the evaluation unit,
  classifying the blood-specific absorption spectra by means of a multiple classification method for determining the sex.

Advantageously, proceeding from the relative position of the pointed and blunt poles with respect to one another, the closed egg is positioned substantially horizontally or substantially vertically with the pointed pole upward.

Likewise advantageously, candling by the light source is realized above, below and/or to the side of the positioned egg.

Moreover, it is advantageous if at least one LED, a fluorescent lamp, a broadband supercontinuum white light laser, a tunable laser and/or a halogen lamp are used as a light source.

Advantageously, use is made of a light source with a spectral range from UV light to NIR light, particularly advantageously use being made of a light source with a spectral range from 350 to 900 nm.

It is likewise advantageous if a filter is inserted between the light source and the egg.

It is also advantageous if the light source is simultaneously used as excitation unit.

Moreover, it is advantageous if the position data relating to the cardiovascular system are calculated by segmenting the generated camera image.

It is likewise advantageous if the blood-specific and/or blood-extrinsic absorption spectra are captured by means of a spectrometer, diodes and/or an HSI camera and/or an FPA detector, together with at least one lens.

It is particularly advantageous if, during or following the capture of the cardiovascular system, a measuring unit for determining the diameter of the cardiovascular system is introduced only through a pore in the eggshell with a diameter of ≤1 mm.

It is furthermore advantageous if mathematical, physical or chemical methods are used to compensate the blood-extrinsic absorption spectra.

Likewise advantageously, the compensation of the blood-extrinsic signals in the spectra is realized by forming spectroscopic differences, wherein the difference is formed from spectra with blood-specific and blood-extrinsic absorption spectra and spectra with blood-extrinsic absorption spectra.

And, advantageously, complementary sex-specific signals are used for the classification, wherein, very particularly advantageously, the classification is carried out by forming ratios of the complementary sex-specific signals.

Advantageously, the method is realized between the $3^{rd}$ and $4^{th}$ incubation day.

According to the invention, a method is provided which, simultaneously, realizes the determination of fertilization and sex in ovo on a closed egg, facilitates the determination of fertilization and sex during incubation time period and facilitates a great accuracy in the fertilization rates and sex determination.

Within the scope of the present invention, the method for determining fertilization and sex in ovo should be performed on closed eggs, egg according to the invention intending to mean any egg with a protective sleeve, the latter being an eggshell, in particular. In particular, eggs where the method according to the invention is used include birds' eggs and reptile eggs, with chicken eggs being examined in particular. Furthermore, a virtually closed egg should be understood to mean an egg with a pore ≤1 mm in the eggshell and intact outer and inner shell membrane since such pores without an additional seal do not impair the further embryonal development.

By way of the method according to the invention, the spectroscopic sexing occurs at a very early development stage of the egg by way of the analysis of spectra in the embryonal blood and multiple classification algorithms are used for a subsequent evaluation of the optical signals obtained from the analysis.

Spectra obtained by means of absorption-spectroscopic analyses, the so-called absorption spectra, are understood to mean all registered signals that are reflected, non-elastically scattered or transmitted by the egg. The interconnected processes of transmission, absorption and attenuation, each of which can be assigned a label for a spectrum, are subsumed here by the term absorption spectra.

The eggs are positioned in a first method step. Here, the positioning of the cardiovascular system of the embryo under the eggshell is set by turning the egg out of the incubator position.

In principle, the spectroscopic determination of fertilization and sex can be carried out in any egg position.

However, the horizontal positioning of the egg, where pointed and blunt poles of the egg lie horizontally opposite one another, or the positioning of the egg with the pointed pole at the top are preferred. In these positions of the egg, the cardiovascular system is directly below the eggshell since density differences form between the individual components in the egg during the first incubation days as a result of metabolic processes. As a result of these, the yoke-adhering embryo including the extra-embryonal vessels is always situated at the highest point within the egg in the case of an egg rotation. If the egg is left in the incubation position, as applied during regular incubation management in a commercial hatchery (blunt egg pole directed upward; pointed egg pole directed downward), then an air chamber will be situated between the embryo including the embryonal cardiovascular system and the eggshell.

The analysis of the closed pointed egg pole is a particularly advantageous embodiment of the method according to the invention as the eggs can be turned very easily in large numbers in commercially used egg racks. A further advantage of this positioning consists of the fact that the eggshell area under which the embryo with the blood vessel network can be situated is reduced at the pointed pole in relation to the eggshell area in the case of a horizontal egg position as a result of the more pronounced curvature of the shell. This leads to a reliable and faster detection of the cardiovascular system and shorter motor travels of the detecting optical unit.

After the at least one egg has been positioned, said egg is illuminated or candled by means of a light source using light in the spectrum of visible and/or near-infrared light.

Within the scope of the invention, illuminating the egg should be understood to mean the registration of the absorption spectra, preferably in the transflection mode.

Within the scope of the invention, candling the egg should be understood to mean the registration of the absorption spectra, preferably in the transmission mode.

This method step of illuminating or candling the egg serves to find the cardiovascular system by means of an optical recording system, in particular by means of a camera.

Within the electromagnetic spectrum, the light spectrum comprises all components of the spectrum visible to the human, with wavelengths between approximately 400 and approximately 700 nm. The light source used according to the invention can emit light in the light spectrum. Provided the optical recording systems are equipped in this respect, the light source could also emit light in the range of ultraviolet and/or infrared spectra. What is decisive is that the cardiovascular system in the egg is found using the optical recording system.

In principle, the light source could be positioned and arranged on all sides of the positioned egg, for example below the egg, to the side of the egg or above the egg. A broadband light source is advantageously used as a light source, for example LEDs, fluorescent lamps, gas discharge lamps, broadband supercontinuum white light lasers or halogen lamps with filters, the filters serving to avoid too much thermal radiation on the positioned egg.

An image is recorded by means of an optical recording system arranged above the egg, advantageously by means of a camera system, while the positioned egg is illuminated or candled by means of a light source. The recording system registers an image of the embryo and the cardiovascular system. Once the image has been recorded, the image data are evaluated, with the position data for the cardiovascular system being ascertained, for example by way of segmentation. These position data are transmitted to a centering unit and are used to position the detection unit above the cardiovascular system and, in the case of the transflection process, the excitation unit as well. Should a cardiovascular system not be detectable in the egg, the egg can be rejected as unfertilized. Hence, the fertilization has already been determined in this method step.

The light source for illuminating or candling the egg can simultaneously represent the excitation unit. This is the case when the transmission process is applied, in which the egg is candled by way of the light source from below and/or from the side for the purposes of capturing the position data of the cardiovascular system, and said egg is consequently arranged opposite or at a certain angle to the optical recording system and the detection unit. In this arrangement, the light source arranged below the egg and/or to the side of the egg represents the excitation unit at the same time.

In contrast thereto, the egg can firstly be candled from below for the purposes of capturing the position data of the cardiovascular system and secondly an excitation unit can be arranged thereabove, said excitation unit likewise representing a light source, in the case of which the radiation of the excitation unit is reflected and detected from/to the detection unit (transflection).

In principle, the cardiovascular system can be found directly in the egg using an HSI camera or a focal plane array (FPA) detector. To this end, it is advantageous if use is made of an HSI camera with a wide-angle lens and/or a large array detector in order to be able to register the entire egg surface at which the embryo and the cardiovascular system are situated. However, processing the three-dimensional data record of the HSI camera or of the FPA detector in the evaluation unit is more time-consuming than recording an RGB or monochrome image, which is why coupling such a vision system with an HSI camera or an FPA detector represents a technically advantageous solution.

Following the positioning of the detection unit and the excitation of the blood situated in the cardiovascular system by means of an excitation unit, the blood-specific and blood-extrinsic absorption spectra are detected and selected, wherein the blood is excited by means of excitation light transmitted through the cardiovascular system or excitation light transflected through the blood vessels.

The detected absorption spectra can be divided into two groups a) and b):
(a) spectra which are composed of blood-specific information and blood-extrinsic information and
(b) spectra only containing blood-extrinsic information.

However, spectra could also consist of blood-specific information only.

The absorption spectra of the blood are registered in the spectral ranges from UV light to NIR light, but preferably in the spectral range of 350 to 900 nm, on the closed egg and, in the subsequent evaluation of the absorption spectra, the optical signals of all egg constituents surrounding the cardiovascular system and hence being blood-extrinsic, including the eggshell, are removed by optical, biochemical and/or mathematical compensation.

Surprisingly, it was found that the diameter of the cardiovascular system has an influence on the results of the blood-extrinsic absorption spectra and taking account of the diameter leads to further improvement in the accuracy when identifying the sex.

By measuring the diameter of the captured cardiovascular system, the "layer thickness" is ascertained and the absorption is objectified within the spectroscopic-analytic sense as per Lambert-Beer's law. By way of example, the diameter can be determined by optical coherence tomography by way of the same or a further optical system. However, other optical interference methods could likewise be used.

To achieve an improved resistance to interference and higher accuracy when identifying the sex in a particularly advantageous configuration of the method, it is possible, during or following the capture of the cardiovascular system, for a measuring unit for determining the diameter of the captured cardiovascular system to be introduced through a pore, which has only been introduced in the eggshell and which has a diameter of $\leq 1$ mm.

The extremely small diameter of the pore of $\leq 1$ mm leads to the pore healing and sealing on its own accord after the measuring unit has been removed. Therefore, as a result of introducing the pore in the eggshell only, the egg itself is not considered to be an "opened egg", and so the embryonal development is not influenced, as is known when opening the egg like in the prior art.

According to the invention, the advantage of the particularly small hole of $\leq 1$ mm lies in the fact that a measuring unit, for example in the form of an optical fiber with a diameter of less than 1 mm, can be guided through the pore up to the shell membrane which has remained intact, and so optical effects of the eggshell (e.g., fluorescence, Rayleigh scattering) are not captured as well. Moreover, a further advantage lies in the registration of absorption spectra and/or fluorescence light of the blood for sexing, which is rendered possible therewith. In the case of the completely closed eggshell, the fluorescence light of the blood would be superposed by the fluorescence and absorption of the eggshell.

In an advantageous embodiment of the method, the transmitted excitation light is detected by means of an HSI camera or FPA detector, by means of which it is possible to measure a spectral, three-dimensional image stack. Here, the HSI camera or the FPA detector is positioned in accordance with the position data of the camera system in such a way that the x*y imaging area includes both positions (a) within and (b) outside of the blood vessels, with it being possible to assign to each picture element of the x*y imaging area an absorption spectrum at this picture element.

A further preferred embodiment is the detection of the excitation light by means of a detector row, an HSI camera or FPA detector, in which only a row x or column y is registered, with this row/column likewise having to include positions (a) within and (b) outside of the blood vessels. This embodiment has the technical advantage of realizing a faster throughput within the scope of sexing, with a simpler construction from a technical point of view as a result of motor travels in one direction only.

From the image, the row/column or individual measurement points, the blood-specific absorption spectra which contain (a) sex-specific information of the embryonal blood are selected following the recording from those (b) of the blood-extrinsic constituents (egg white, yoke, inner and outer shell membrane, eggshell) outside of the blood vessels.

Blood-extrinsic absorption spectra are compensated by selecting spectral signals of the blood from all detected absorption spectra of the egg.

Within the method according to the invention, the absorption spectra are detected in such a way that at least one absorption spectrum, but preferably a plurality of absorption spectra, of group (a) and at least one absorption spectrum, but preferably a plurality of absorption spectra, of group (b) are detected.

Individual point measurements within the position of the blood vessels (group (a)) and outside of the position of the blood vessels (group (b)) are carried out by virtue of a microscope optical unit being focused into a blood vessel and outside of a blood vessel and the spectra being detected using a spectrometer.

The spectra which, in addition to the blood-extrinsic absorptions of the constituents of the egg (yoke, egg white, egg membranes and eggshell), have the absorption spectra of the embryonal blood are selected from the total number of detected absorption spectra.

The group of non-selected absorption spectra only contain spectral signals of all further constituents of the egg but contain no information about the embryonal blood. The compensation of the absorption signals of the further constituents of the egg surrounding the blood vessels is facilitated by, e.g., mathematical operations on the two groups, for example by means of forming spectroscopic differences. Here, forming a spectroscopic difference is understood to mean the subtraction of a spectroscopic background, from which, mathematically, a ratio of the intensity values arises.

The classification of the blood-specific absorption spectra, and hence also the sex-specific absorption spectra, is implemented by means of a multiple classification method, wherein, following the capture of the sex-specific absorption spectra and the data pre-processing of the blood-specific absorption spectra, a multiple classification method with at least two different methods of data pre-processing of the spectra and of the method for classification assigned to the respective data pre-processing is advantageously carried out.

The technical effects and the advantages over the prior art set forth below are obtained using the method according to the invention.

Surprisingly, it was found that the absorption spectra of the blood are sex-specific and also remain as such during the development of the embryo. Thus, it is possible for the first time to determine fertilization and sex on the closed egg by means of the absorption of the blood-specific spectra while taking account of the compensation of the further constituents of the egg. The method according to the invention uses small but sex-specific differences in the molecular structure of the hemoglobin for sexing. Here, this is not based only on capturing signals originating from the central structure element, the porphyrin ring, but rather based also on information about intramolecular shifts in the electron density and energy states by the substituents and side groups.

A substantial advantage of the method according to the invention is that fertilization and sex are determined on the closed egg. This can dispense with the complicated opening and closing of the egg, known from the prior art, and leads to substantially reduced costs of the method. Likewise, it is not necessary to pretreat the eggshell in order to make the latter more transparent for subsequent examination. In particular, the embryonal development remains uninfluenced by the determination of fertilization and sex, carried out on the closed egg, moreover leading to improved hatching rates.

Intensive, sex-specific optical signals from the embryonal blood are obtained by the first-ever use of absorption spectra from blood vessels of the closed egg only. In relation to previously known Raman-spectroscopic methods and examinations, this obtains a substantially improved signal quality with a low error rate when determining the sex.

Moreover, according to the invention, a high classification accuracy is achieved by the compensation of strong absorptions of the egg constituents of the egg which surround the blood vessels and make no contribution to the fertilization and sex analysis. As a result, the classification is stable and independent of the natural variability of the eggs and the variability of the incubation process.

A substantial further advantage of the invention over other methods known from the prior art consists of the fact that, in particular, sexing is carried out reliably and with very high accuracy at a very early stage and over a long period of time following the incubation since the sex-specific absorption spectra of the embryonal blood remain constant during incubation in contrast to the information of the further constituents of the egg. This is precisely not the case for the other constituents of the egg, such as the yoke or the egg white.

Moreover, it is possible to carry out the measurement of the sex-specific absorption signals on the closed egg in combination with sex-specific fluorescence signals. What needs to be taken into account here is that the fluorescence of the shell has to be advantageously compensated, either mathematically by way of registered reference spectra of the shell or else by optical or chemical quenching. An advantage of measuring the sex-specific absorption signals in combination with sex-specific fluorescence signals on the closed egg within a self-sealing pore ≤1 mm is that there is no need to take account of optical effects of the eggshell.

Moreover, a multiplicity of optical combination options arise for this method from the aforementioned various positionings, light sources for the camera, excitation sources for the absorption and, possibly, for the fluorescence and detectors so that unchanging and reliable analysis results are obtained despite the variability of the arrangement of the components to be used.

A further advantage of the method according to the invention is that complementary sex-specific signals can be used for the classification of the blood-specific absorption spectra.

Within the scope of the invention, complementary sex-specific signals are understood to mean that the spectral intensities of female and male embryonal blood show reverse at different wavelengths.

Thus, it was surprisingly found that high intensities can be observed in males ($I_{male\_sw}$) and low intensities can be observed in females ($I_{female\_sw}$) in the shortwave spectral range, while a low intensity occurs in males ($I_{male\_lw}$) and a high intensity occurs in females ($I_{female\_lw}$) in the longwave spectral range. Advantageously, the ratio of $I_{female\_sw}$ to $I_{female\_lw}$ or the ratio of $I_{male\_sw}$ to $I_{male\_sw}$ is formed for a reliable classification. As a result, it is possible to obtain a variable for the classification that is independent of the absolute intensity.

BRIEF DESCRIPTION OF THE DRAWINGS

The invention will be explained in more detail below on the basis of two exemplary embodiments. Herein.

DETAILED DESCRIPTION OF THE PREFERRED EMBODIMENTS

Exemplary Embodiment 1

Figure 2:
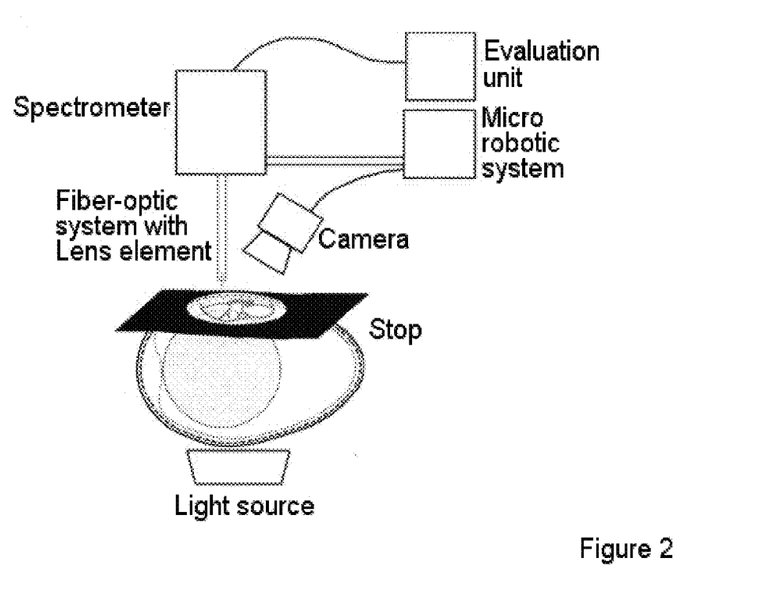
FIG. 2 shows the optical setup in the transmission mode for measuring the sex-specific absorption of the embryonal blood by means of a spectrometer-coupled optical fiber in the case of horizontal bearing of the egg.

A chicken egg is taken from the incubator after 3.5 incubation days, turned from the incubation position through 90° and positioned at a distance of approximately 4 cm above a halogen lamp, which has a controllable power between 0 and 50 W and an emission spectrum in the spectral range between 400 and 900 nm. Situated in the upper half of the egg curvature of the egg to be measured there is a stop with an elliptical opening, which prevents excitation light striking the detector directly and the saturation of the detector unit connected therewith. The egg is candled after the halogen lamp has been switched on and the embryo with the blood vessel network becomes visible. Now, the egg was positioned in such a way that the embryo and the extra-embryonal blood vessels are at least partly situated within the stop aperture. The green channel of an RGB camera is used to capture the positions of the heart structure within the embryo and the extra-embryonal blood vessel network. The camera image obtained is segmented and the position data are transferred to a customer-specific micro robotic system. This system now transports a fiber-optic system by Grintech, consisting of a multimodal fiber and a micro grin lens element (diameter d=0.5 mm) to the embryonal heart in accordance with the position data, with the positioning having been implemented at a work distance of 0.5 mm from the shell and at an angle of 90° with respect to the shell tangent. The fiber of the fiber-optic system is coupled to a UV/VIS spectrometer by Ocean Optics and an absorption spectrum in the spectral range between 480 and 900 nm is registered. There is second positioning of the optical fiber with a subsequent registration of a spectrum within the stop aperture but outside of all segmented blood vessel positions and the heart position. After the two measurements have been completed, the difference spectra are formed in the evaluation unit and subject to multiple data pre-processing. Consequently, mean value difference spectra are obtained for male and female embryonal blood.

Figure 1:
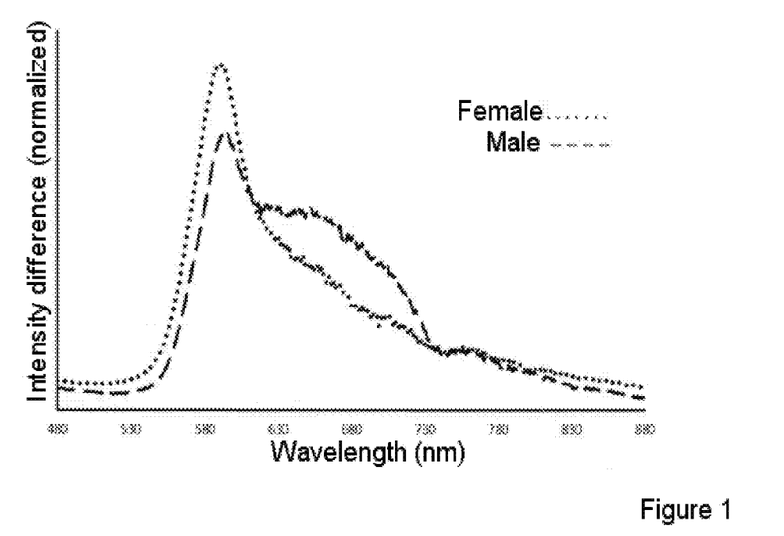
FIG. 1 shows in-ovo mean value absorption spectra of embryonal blood, measured in closed chicken eggs after 3.5 days of incubation, after subtracting the further constituents of the closed egg.

It is clearly evident from FIG. 1 that there is a point of intersection between the male and female mean value spectrum at approximately 610 nm, and hence that there is a wavelength-dependent sex-specific intensity reversal.

Following internal referencing of the wavelength-dependent, sex-specific intensity, the final sexing was able to be implemented on the basis of the sex-specific signals in the wavelength range of 500-900 nm by means of multiple classification algorithms.

Exemplary Embodiment 2

Figure 3:
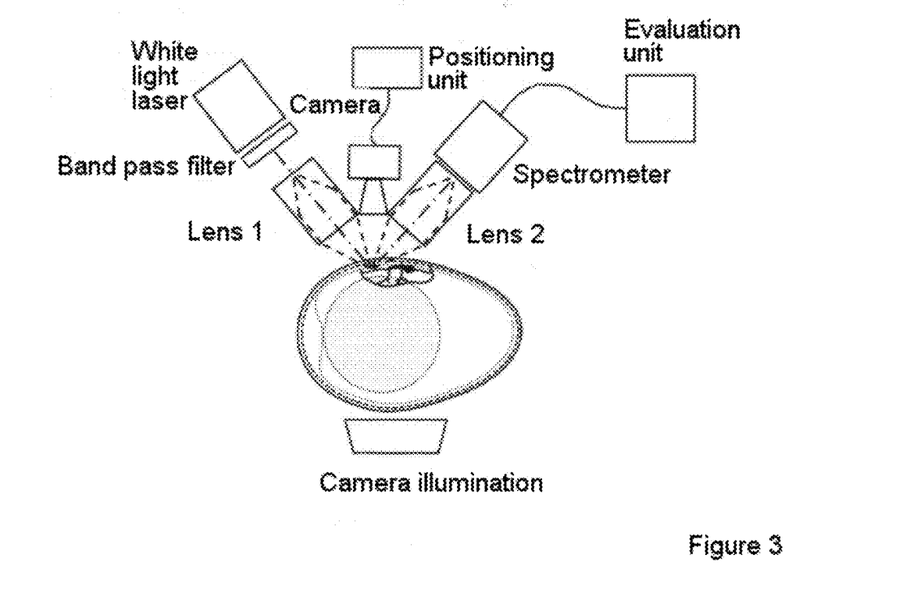
FIG. 3 shows the optical setup in the transflection mode for measuring the sex-specific absorption of the embryonal blood.
Figure 4:
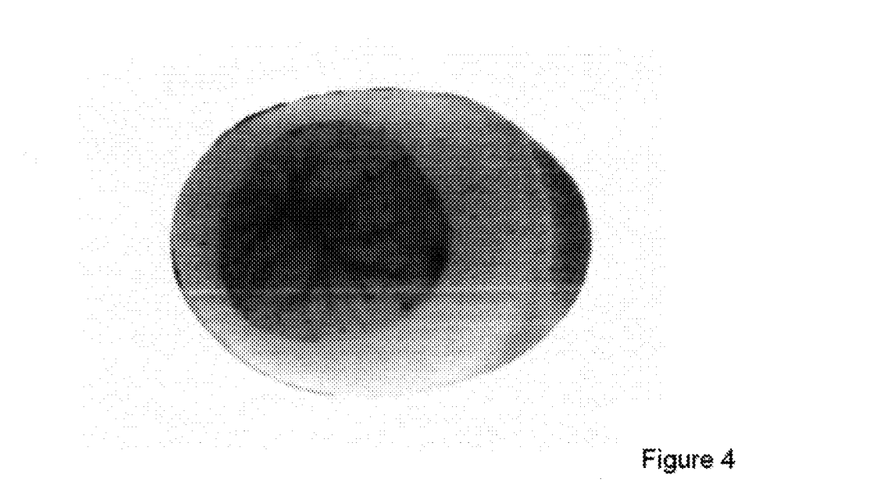
FIG. 4 shows an HSI image recording of a chicken egg that has been incubated for 3.5 days and contains embryonal cardiovascular structures.

A chicken egg is taken from the incubator after 3.5 incubation days, turned from the incubation position through 90° and positioned at a distance of approximately 1 cm above an LED lamp, which has light in the spectral range between 400 and 730 nm. The egg is candled after the LED lamp has been switched on and the embryo with the blood vessel network becomes visible. The green channel of an RGB camera is used to capture the positions of the heart structure within the embryo and the extra-embryonal blood vessel network. The camera image obtained is segmented and the position data are transferred to a customer-specific micro robotic system. These position data are used to position a lens 1 (NA=0.4, WD=20 mm, magnification 20-fold, by Mitutoyo) such that the excitation light of a supercontinuum white light laser (NKT Photonics), filtered by a bandpass filter in the spectral range of 450-600 nm, is focused at the embryonal heart structure. The position data of the robotic system is used to likewise position a second lens over the heart structure in such a way that the transflected, backscattered signal is collected and, via free beam optics, directly focused in the input slit of a UV/VIS spectrometer (FLAME, Ocean Optics), in which the absorption signals are registered. There is second positioning of the two microscope lenses with subsequent registration of a spectrum outside of all segmented blood vessel positions and the heart position. After the two measurements have been completed, the difference spectra are formed in the evaluation unit and subject to multiple data pre-processing. The final sexing is implemented on the basis of the sex-specific signals in the emission spectral range by means of multiple classification algorithms.

The invention claimed is:

1. A method for determining fertilization and sex in ovo on a closed egg, only containing natural pores, comprising the method steps of: a) positioning the closed egg, b) candling and/or illuminating the egg by means of at least one light source using light in the spectrum of visible and/or near-infrared light, c) recording an image of the candled and/or illuminated closed egg by means of an optical recording system and evaluating captured data of a generated image by means of an evaluator, d) calculating a position of a cardiovascular system situated in the egg from the evaluated data of a camera image by means of the evaluator, e) setting a detector above the calculated position of the cardiovascular system by means of a positioner, f) exciting blood situated in the cardiovascular system by means of an exciter, g) detecting and selecting blood-specific absorption spectra and blood-extrinsic absorption spectra by means of a capturer, h) determining fertilization, wherein the following method steps are performed after fertilization has been established, i) compensating the spectra with blood-extrinsic information by a compensation method by means of the evaluator, j) classifying the blood-specific absorption spectra by means of a multiple classification method for determining sex.

2. The method as claimed in claim 1, wherein, proceeding from a relative position of pointed and blunt poles with respect to one another, the closed egg is positioned substantially horizontally or substantially vertically with the pointed pole upward.

3. The method as claimed in claim 1, wherein candling by the light source is realized above, below and/or to the side of the positioned egg.

4. The method as claimed in claim 1, wherein at least one LED, a fluorescent lamp, a broadband supercontinuum white light laser, a tunable laser and/or a halogen lamp are used as the light source.

5. The method as claimed in claim 1, wherein the light source has a spectral range from UV light to NIR light.

6. The method as claimed in claim 5, wherein the light source has a spectral range from 350 to 900 nm.

7. The method as claimed in claim 1, wherein a filter is inserted between the light source and the egg.

8. The method as claimed in claim 1, wherein the light source is simultaneously used as the exciter.

9. The method as claimed in claim 1, wherein the position data relating to the cardiovascular system are calculated by segmenting the generated camera image.

10. The method as claimed in claim 1, wherein the blood-specific and/or blood-extrinsic absorption spectra are captured by means of a spectrometer, diodes and/or an HSI camera and/or an FPA detector, together with at least one lens.

11. The method as claimed in claim 1, wherein, during or following the capture of the cardiovascular system, a measurer for determining the diameter of the cardiovascular system is introduced only through a pore in the eggshell with a diameter of ≥1 mm.

12. The method as claimed in claim 1, wherein sexing is realized by means of absorption signals and/or fluorescence signals through a pore ≥1 mm in the egg.

13. The method as claimed in claim 1, wherein mathematical, physical or chemical methods are used to compensate the blood-extrinsic absorption spectra.

14. The method as claimed in claim 13, wherein the compensation of the blood-extrinsic signals in the spectra is realized by forming spectroscopic differences, wherein the difference is formed from spectra with blood-specific and blood-extrinsic absorption spectra and spectra with blood-extrinsic absorption spectra.

15. The method as claimed in claim 1, wherein complementary sex-specific signals are used for the classification.

16. The method as claimed in claim 15, wherein the classification is performed by means of a combination/logical linking of the complementary sex-specific signals by way of mathematical methods, particularly advantageously by forming ratios.

17. The method as claimed in claim 1, wherein the method is realized between a $3^{rd}$ and $4^{th}$ incubation day.

* * * * *